(12) United States Patent
Bhatt et al.

(10) Patent No.: US 10,206,669 B2
(45) Date of Patent: Feb. 19, 2019

(54) SYSTEM, METHOD, AND APPARATUS FOR ASSISTING WITH SUBMUCOSAL DISSECTIONS

(71) Applicant: THE CLEVELAND CLINIC FOUNDATION, Cleveland, OH (US)

(72) Inventors: Amit Bhatt, Shaker Hts., OH (US); Shengqiang Gao, Beachwood, OH (US); William Kolosi, Stow, OH (US); John Vargo, University Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 15/409,761

(22) Filed: Jan. 19, 2017

(65) Prior Publication Data
US 2017/0209132 A1    Jul. 27, 2017

Related U.S. Application Data

(60) Provisional application No. 62/293,505, filed on Feb. 10, 2016, provisional application No. 62/281,215, filed on Jan. 21, 2016.

(51) Int. Cl.
*A61B 17/02* (2006.01)
*A61B 17/00* (2006.01)
*A61B 17/064* (2006.01)

(52) U.S. Cl.
CPC .......... *A61B 17/02* (2013.01); *A61B 17/0218* (2013.01); *A61B 2017/0034* (2013.01); *A61B 2017/00269* (2013.01); *A61B 2017/00336* (2013.01); *A61B 2017/00862* (2013.01); *A61B 2017/00867* (2013.01);
(Continued)

(58) Field of Classification Search
CPC ...................................... A61B 17/02–17/0293
USPC .................................................. 600/201–246
See application file for complete search history.

(56) References Cited

U.S. PATENT DOCUMENTS 5,509,923 A    4/1996 Middleman et al.
5,512,037 A    4/1996 Russell et al.
(Continued)

FOREIGN PATENT DOCUMENTS

EP    2578167 A1    10/2013
JP    2005103107    4/2005
WO    201254845 A1    11/2012

OTHER PUBLICATIONS

International Search Report corresponding to the International App. No. PCT/US2017/014038, dated Apr. 5, 2017, 5 pages.
(Continued)

*Primary Examiner* — Nicholas J Plionis
(74) *Attorney, Agent, or Firm* — Carter, DeLuca, Farrell & Schmidt, LLP

(57) ABSTRACT

Systems, methods, and apparatuses for assisting with submucosal dissections include a retraction strip body. The retraction strip body is formed at least partially from a deformable material. The retraction strip body is capable of being selectively moved between a first condition and a second condition. In the first condition, the retraction strip body is capable of engaging a target patient tissue. In the second condition, the retraction strip body is capable of retracting the target patient tissue. At least one tissue engagement member is located on the retraction strip body.

15 Claims, 7 Drawing Sheets

(52) U.S. Cl.
CPC ............... *A61B 2017/00946* (2013.01); *A61B 2017/0225* (2013.01); *A61B 2017/0649* (2013.01)

(56) References Cited

U.S. PATENT DOCUMENTS

| | | | | |
|---|---|---|---|---|
| 8,187,315 B1* | 5/2012 | Clauson | ................ | A61B 17/02 623/1.1 |
| 2012/0289776 A1* | 11/2012 | Keast | ................... | A61B 1/2676 600/106 |

OTHER PUBLICATIONS

Australian Examination Report issued in corresponding Appl. No. AU 2017209092, dated Nov. 30, 2018 (5 pages).

* cited by examiner

SYSTEM, METHOD, AND APPARATUS FOR ASSISTING WITH SUBMUCOSAL DISSECTIONS

RELATED APPLICATION

This application claims priority from U.S. Provisional Application No. 62/293,505, filed 10 Feb. 2016, and U.S. Provisional Application No. 62/281,215, filed 21 Jan. 2016, the subject matter of both of which is incorporated herein by reference in its entirety.

TECHNICAL FIELD

This disclosure relates to an apparatus, method, and system for assisting with submucosal dissections and, more particularly, to a tissue retraction device and method for use.

BACKGROUND

Endoscopic submucosal dissection ("ESD") is an endoscopic technique in which a lesion, such as, but not limited to, an early gastrointestinal cancer, is endoscopically dissected. One of the challenges in performing an ESD is the lack of a second hand that can provide traction and counter-traction as in conventional surgery. Delivering a device that may act like the second hand of a surgeon could make ESDs more efficient to perform.

SUMMARY

In an aspect, a tissue retraction device is provided. The tissue retraction device includes a retraction strip body. The retraction strip body is formed at least partially from a deformable material. The retraction strip body is capable of being selectively moved between a first condition and a second condition. In the first condition, the retraction strip body is capable of engaging a target patient tissue. In the second condition, the retraction strip body is capable of retracting the target patient tissue. The tissue retraction device includes at least one tissue engagement member. The tissue engagement member is located on the retraction strip body.

In an aspect, a method for assisting with submucosal dissections is provided. A tissue retraction device is provided. The tissue retraction device includes a retraction strip body. The retraction strip body is formed at least partially from a deformable material. The retraction strip body is capable of being selectively moved between a first condition and a second condition. In the first condition, the retraction strip body is capable of engaging a target patient tissue. In the second condition, the retraction strip body is capable of retracting the target patient tissue. The tissue retraction device includes at least one tissue engagement member. The tissue engagement member is located on the retraction strip body. The tissue retraction device includes an endoscope. The endoscope has an endoscope proximal end and an endoscope distal end. The endoscope has an endoscope lumen that extends longitudinally between the endoscope proximal end and the endoscope distal end. The endoscope is inserted into a patient. The endoscope distal end is positioned at a target patient tissue site adjacent to the target patient tissue. The retraction strip body is selectively moved into the first condition. With the retraction strip body in the first condition, the retraction strip body is inserted through the endoscope lumen and out to the target patient tissue site. With the retraction strip body in the first condition, the target patient tissue is engaged with at least one tissue engagement member. The target patient tissue is selectively moved into a retracted position by selectively moving the retraction strip body into the second condition. With the selective movement of the retraction strip body from the first position to the second position, the tissue engagement member is caused to responsively move the target patient tissue from its original position to a retracted position.

In an aspect, a system for assisting with submucosal dissections is provided. The system for assisting with submucosal dissections includes a tissue retraction device. The tissue retraction device includes a retraction strip body. The retraction strip body has first and second ends spaced laterally apart. The retraction strip body is formed at least partially from a deformable material. The retraction strip body is capable of being selectively moved between a first condition and a second condition. In the first condition, the retraction strip body is capable of engaging a target patient tissue. In the second condition, the retraction strip body is capable of retracting the target patient tissue. The retraction strip body includes at least two sets of tissue engagement members. A first set of tissue engagement members is located on the retraction strip body first end. A second set of tissue engagement members is located on the retraction strip body second end. The tissue engagement members are at least one of a barb, a clip, a hook, an adhesive, and any other attachment mechanism. The system for assisting with submucosal dissections includes an endoscope and a dissector. The endoscope has a proximal end and a distal end. The endoscope has an endoscope lumen that extends longitudinally between the endoscope proximal end and the endoscope distal end.

BRIEF DESCRIPTION OF THE DRAWINGS

For a better understanding, reference may be made to the accompanying drawings, in which.

DESCRIPTION OF EMBODIMENTS

Unless defined otherwise, all technical and scientific terms used herein have the same meaning as is commonly understood by one of ordinary skill in the art to which the present disclosure pertains.

As used herein, the term "patient" can refer to any warm-blooded organism including, but not limited to, human beings, pigs, rats, mice, dogs, goats, sheep, horses, monkeys, apes, rabbits, cattle, farm animals, livestock, etc.

As used herein, the term "user" can be used interchangeably to refer to an individual who prepares for, assists, and/or performs a procedure.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" can be interpreted to include X and Y.

It will be understood that when an element is referred to as being "on," "attached" to, "connected" to, etc., another element, it can be directly on, attached to, connected to, coupled with or contacting the other element or intervening elements may also be present. It will also be appreciated by those of skill in the art that references to a structure or feature that is disposed "adjacent" another feature may not have portions that overlap or underlie the adjacent feature.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

Figure 1:
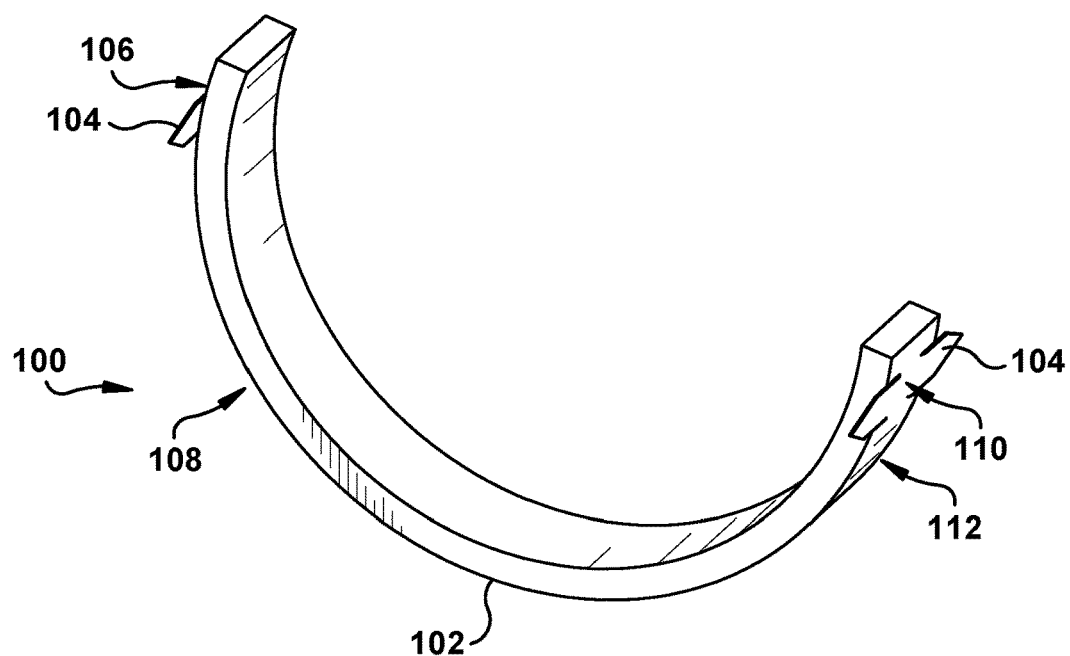
FIG. 1 is a side view of an aspect of the present invention in a first use configuration.

FIG. 1 depicts a tissue retraction device 100. The tissue retraction device 100 includes a retraction strip body 102 and at least one tissue engagement member 104. The tissue engagement member 104 is located on the retraction strip body 102. The tissue engagement member 104 may be at least one of a barb, a clip, a hook, an adhesive, and any other attachment mechanism. A first set of tissue engagement members 106 may be located on a retraction strip body first end 108 and a second set of tissue engagement members 110 may be located on a retraction strip body second end 112. The retraction strip body first and second ends 108, 112 are spaced laterally apart along the retraction strip body 102. The term "lateral" is used herein to indicate a substantially horizontal direction, in the orientation of FIG. 1.

Figure 2:
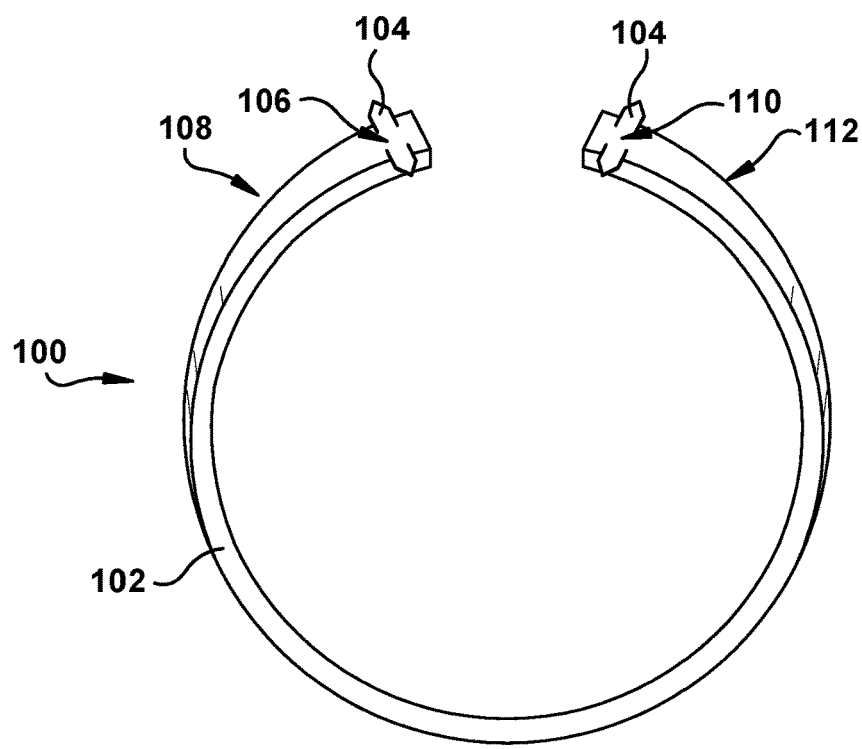
FIG. 2 is a side view of the aspect of FIG. 1 in a second use configuration.

The retraction strip body 102 is formed at least partially from a deformable material. The retraction strip body is capable of being selectively moved between a first condition (as shown in FIG. 1) and a second condition (as shown in FIG. 2). In the first condition, the retraction strip body 102 is capable of engaging a target patient tissue T. The target patient tissue T may be, but is not limited to, a lesion. In the second condition, the retraction strip body 102 is capable of retracting the target patient tissue T.

Figure 3:
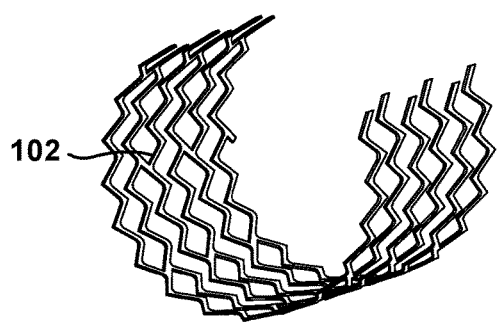
FIGS. 3-9 are side views of the aspect of FIG. 1 in various alternative arrangements.
Figure 4:
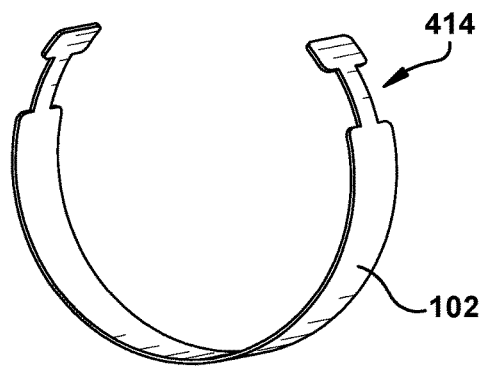
Figure 5:
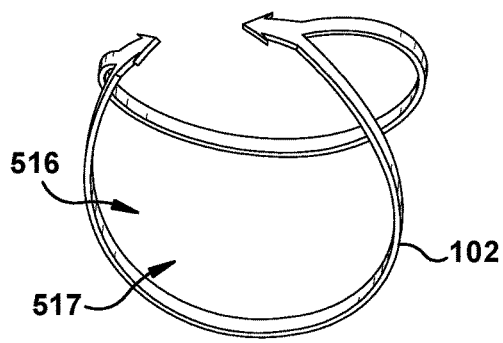
Figure 6:
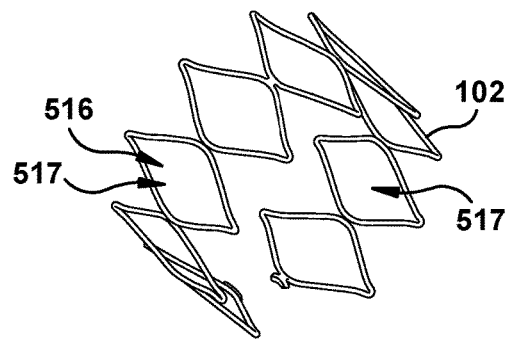
Figure 7:
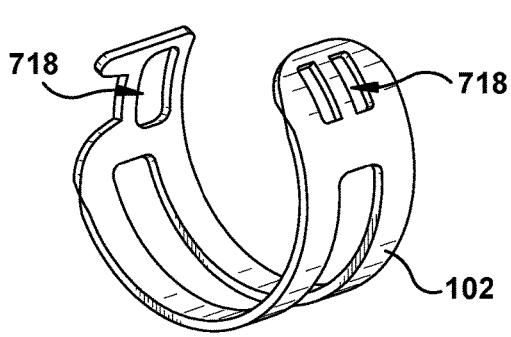
Figure 8:
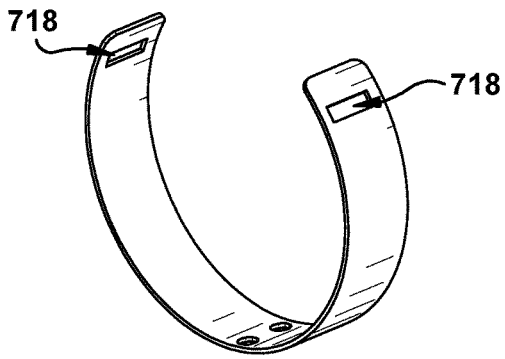
Figure 9:
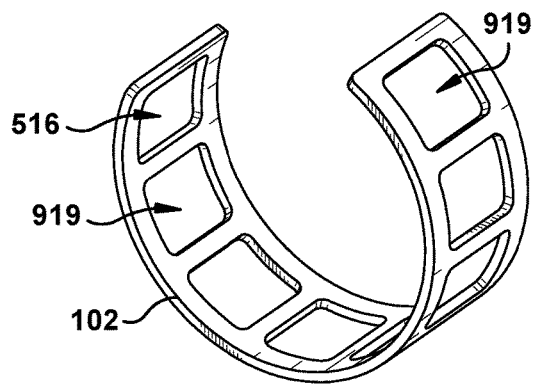

As shown in FIG. 3, the retraction strip body 102 may be a mesh strip. As shown in FIG. 4, the retraction strip body 102 may include at least one indentation 414 on each of the first and second ends to form a "narrow neck" construction. As shown in FIG. 5, the retraction strip body 102 may include an aperture 516, such as, but not limited to a diamond-shaped aperture 517. As shown in FIG. 6, the retraction strip body 102 may include multiple indentations 414 and apertures 516, such as, but not limited to diamond-shaped apertures 517. As shown in FIGS. 7-8, the retraction strip body 102 may include at least one clamping hole 718 that is configured to receive at least a portion of a clamping instrument (not shown), such as, but not limited to, a forceps tip. As shown in FIG. 9, the retraction strip body 102 may include at least one aperture 516, such as, but not limited to, a rectangular aperture 919. The retraction strip body 102 may be diamond-shaped.

The deformable material may be at least partially an elastic material. The elastic material may be at least one of an elastic material, such as, but not limited to, elastic wires, a fabric material, and a shape memory material, such as, but not limited to nitinol. In such case, the transition between the first and second conditions occurs responsive to at least one of an applied force and an elastic deformation of the elastic material retraction strip body 102. The deformable material may be biased to the second condition. A user may apply a force to the elastic material retraction strip body 102 to deform the elastic material retraction strip body 102 to the first condition from the second condition. Upon removal of the applied force, the elastic material retraction strip body 102 automatically moves back to the second condition from the first condition in response to the inherent properties of the shape memory-type elastic material.

Figure 10:
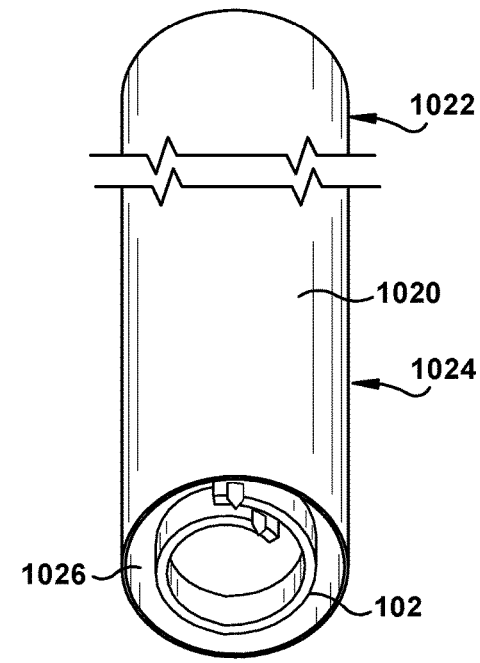
FIG. 10 is a side view of the aspect of FIG. 1 in a third use configuration.

As shown in FIG. 10, the elastic material retraction strip body 102 may be capable of moving into a sheath delivery condition when a sheath 1020 is provided. The elastic material retraction strip body 102 in the sheath delivery condition is shaped to be placed within a sheath lumen 1022 of the sheath 1020. The shape memory material and fabric material retraction strip body 102 in the sheath delivery condition may be rolled onto itself and have a diameter smaller than the diameter of the sheath lumen 1022.

As shown in FIG. 10, the sheath 1020 has a sheath proximal end 1024 and a sheath distal end 1026. The sheath lumen 1022 extends longitudinally between the sheath proximal end 1024 and the sheath distal end 1026. The term "longitudinal" is used herein to indicate a direction substantially perpendicular to the "lateral" direction, and is shown approximately as the vertical direction, in the orientation of FIG. 10.

The deformable material may be at least partially a temperature responsive shape memory material. The temperature responsive shape memory material may be a shape memory alloy, such as, but not limited to, nitinol. The temperature responsive shape memory material retraction strip body 102 may be formed into the second condition as a preset shape above a transition temperature range. The transition temperature range is dependent on the particular ratio of materials, such as metals, forming the temperature responsive shape memory material. Below the transition temperature range, the temperature responsive shape memory material is highly ductile and may be plastically deformed into a desired shape, such as the first condition. Upon reheating above the transition temperature range, the temperature responsive shape memory material returns to its preset shape, such as the second condition.

The deformable material may be at least partially a malleable material. The malleable material retraction strip body 102 is capable of being selectively deformed to, and retained in, at least a selected one of the first and second conditions. A user may deform the malleable material retraction strip body 102 into the first condition and then gradually deform the malleable material retraction strip body 102 to the second condition. The user may cease the deformation of the malleable material retraction strip body 102 at any desired shape between the first condition and the second condition so as to hold the malleable material retraction strip body 102 in a desired shape that is at least partially in the first condition and at least partially in the second condition. In other words, the malleable material retraction strip body 102 may be manually deformed to the first condition, the second condition, or any intermediate condition between the first and second conditions.

The deformable material may be at least partially a flexible stainless steel bistable spring band. In this configuration, the flexible stainless steel bistable spring band retraction strip body 102 may operate similarly to a "slap bracelet," or "slap wrap." A slap bracelet includes a stainless steel bistable spring band that has two positions of operation or two states of being. The first state is the elongated position, such as the first condition of the flexible stainless steel bistable spring band retraction strip body 102. In the first state, the stainless steel bistable spring body retains potential energy. The second state is the coiled state, such as the second condition of the flexible stainless steel bistable spring band retraction strip body 102. The potential energy will cause the band to coil up from the first state to the second state when a force large enough to overcome the resistive forces of the stainless steel bistable spring band is applied to the stainless steel bistable spring band.

Figure 11:
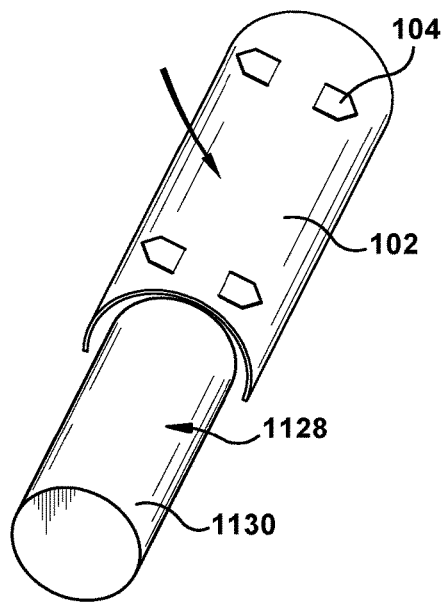
FIG. 11 is a side view of the aspect of FIG. 1 in a fourth use configuration.

The flexible stainless steel spring band retraction strip body 102 in the first condition is shaped to engage a mandrel outer surface 1128 of a mandrel 1130, as shown in FIG. 11. A radially inward force provided by the flexible stainless steel bistable spring band restricts the flexible stainless steel bistable spring band retraction strip body 102 to the mandrel outer surface 1128 when the flexible stainless steel bistable spring band retraction strip body 102 is in the first condition. A mandrel sheath (not shown) may be placed over the mandrel 1130 with attached flexible stainless steel bistable spring band retraction strip body 102 to provide a radially inward force that restricts the flexible stainless steel bistable spring band retraction strip body 102 to the mandrel outer surface 1128. When the retraction strip body is in the first condition, the user may apply a force, depicted as an arrow in FIG. 11, to the flexible stainless steel bistable spring band retraction strip body 102 to urge the flexible stainless steel bistable spring band retraction strip body 102 to move toward the second condition.

The tissue engagement member 104 may be in a flattened condition when the retraction strip body 102 is in the first condition. The tissue engagement member 104 in the flattened condition may be positioned at least partially against the retraction strip body 102. When the tissue engagement member 104 is in the flattened condition, the retraction strip body 102 is capable of being inserted into a target patient tissue site S without engaging the target patient tissue T with the tissue engagement member 104. The tissue engagement member 104 may be in a flared condition when the retraction strip body 102 is at least partially in the second condition. The tissue engagement member 104 in the flared condition is at least partially spaced apart from the retraction strip body 102 so as to be able to engage the target patient tissue T.

Figure 12:
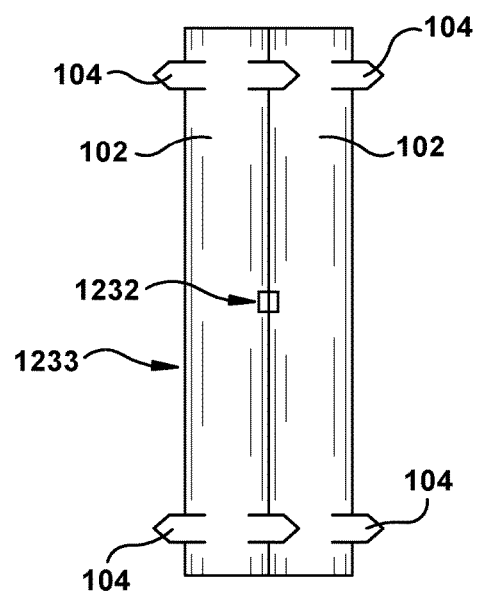
FIG. 12 is a side view of an element of the aspect of FIG. 1.

As shown in FIG. 12, the retraction strip body 102 may have at least one mating member 1232. The mating member 1232 is configured to selectively connect at least two retraction strip bodies 102 together. The connection of at least two retraction strip bodies 102 together may be desirable to increase the effective width of the combined retraction strip body 1233. The combined retraction strip body 1233 may be more desirable than a single retraction strip body 102 in certain situations, such as, but not limited to, when the target patient tissue T is too large to be retracted by a single retraction strip body 102.

Figure 13:
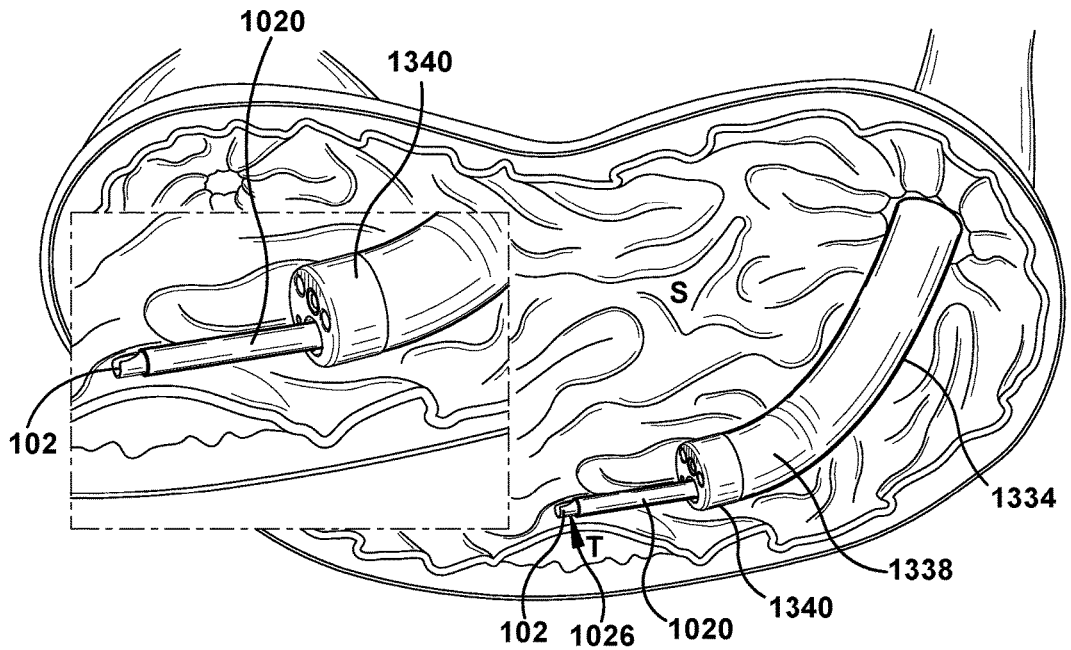
FIGS. 13-17 illustrate an example sequence of operation of the aspect of FIG. 1.
Figure 18:
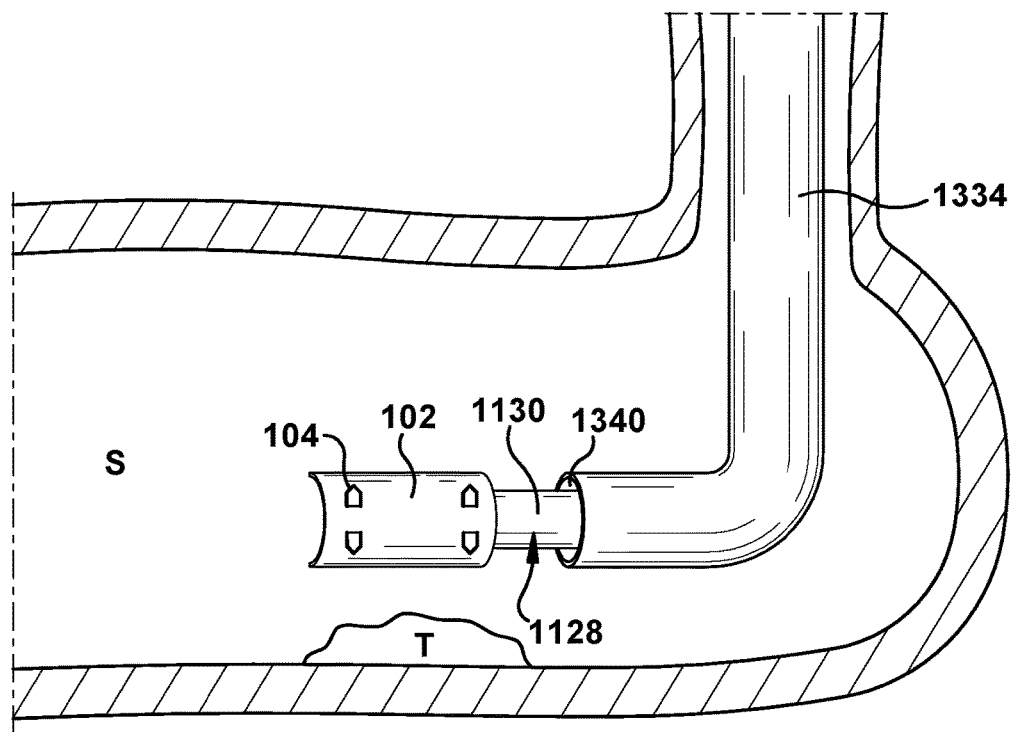
FIG. 18 illustrates an example operation feature of the aspect of FIG. 11.

As shown in FIG. 13, the retraction strip device 100 may include an endoscope 1334. The endoscope 1334 has an endoscope proximal end (not shown) and an endoscope distal end 1338. The endoscope 1334 has an endoscope lumen 1340 that extends longitudinally between the endoscope proximal end (not shown) and the endoscope distal end 1338. At least one of the mandrel 1130 with attached retraction strip body 102 and the mandrel sheath (not shown) may be configured to have a diameter smaller than the diameter of an endoscope lumen 1340, as shown in FIG. 18. The sheath 1020 may be configured to have a diameter smaller than the diameter of an endoscope lumen 1340, as shown in FIG. 13.

The below description describes the use of the sheath 1020 and the elastic material retraction strip body 102, for exemplary purposes. It should be understood that any of the deformable material retraction strip bodies 102 described above, such as the temperature responsive shape memory material retraction strip body 102, the malleable material retraction strip body 102, and the stainless steel bistable spring band retraction strip body 102, may be used in a similar sequence of operation. Further, it should be understood that the any of the retraction strip bodies 102 described above may be delivered to the target patient tissue site S with or without the use of the sheath 1020.

In use, a tissue retraction device 100, as described above, is provided to the user. The endoscope 1334 may be inserted into a patient. The endoscope distal end 1338 is positioned at a target patient tissue site S adjacent to the target patient tissue T, as shown in FIG. 13.

The elastic material retraction strip body 102 may be moved into the sheath condition. The elastic material retraction strip body 102 may be moved into the sheath delivery condition by the user rolling the elastic material retraction strip body 102 onto itself until the elastic material retraction strip body 102 has a smaller diameter than the diameter of the sheath lumen 1026. With the elastic material retraction strip body 102 in the sheath delivery condition, the elastic material retraction strip body 102 is placed within the sheath lumen 1026. The radially inward force of the sheath lumen 1026 restricts the elastic material retraction strip body 102 to the sheath delivery condition.

Figure 14:
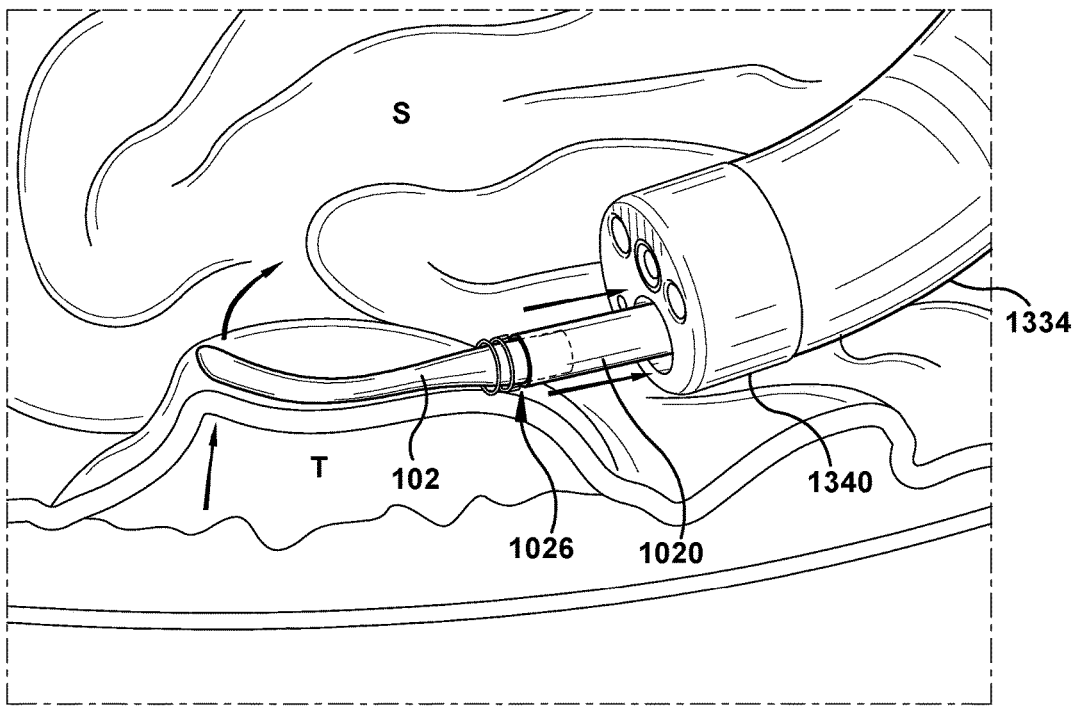

As shown in FIG. 13, with the elastic material retraction strip body 102 in the sheath delivery condition, the sheath 1020 with the attached elastic material retraction strip body 102 is advanced to the target patient tissue site S through the endoscope lumen 1340. As shown in FIG. 14, the sheath 1020 may be retracted, depicted as arrows, from at least one of the target patient tissue site S and the endoscope 1334 with the elastic material retraction strip body 102 remaining at the target patient tissue site S. The retraction of the sheath 1020 may cause the elastic material retraction strip body 102 to responsively move to the first condition. The removal of the radially inward force provided by the sheath lumen 1026 may cause the elastic material retraction strip body 102 to move (e.g., unravel) into the first condition.

Figure 15:
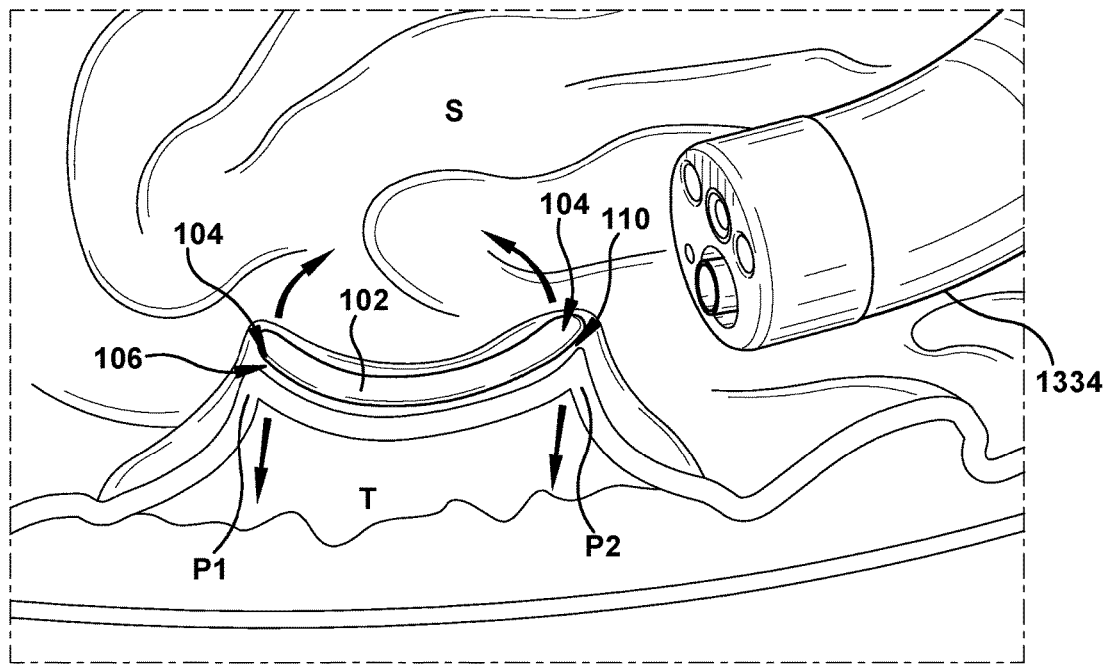

As shown in FIG. 15, with the elastic material retraction strip body 102 in the first condition, the target patient tissue T is engaged with at least one tissue engagement member 104. The first set of tissue engagement members 106, when provided, may be engaged to a first anchoring point P1 on the target patient tissue T, such as, but not limited to, schemes including a barb being inserted into the first anchoring point P1, a clip being attached to the first anchoring point P1, a hook being connected to the first anchoring point P1, an adhesive being attached to the first anchoring point P1, any other suitable attachment mechanism, or any combination thereof. The second set of tissue engagement members 110, when provided, may be engaged to a second anchoring point P2 that is spread apart from the target patient tissue T, such as, but not limited to, schemes including a barb being inserted into the second anchoring point P2, a clip being attached to the second anchoring point P2, a hook being connected to the second anchoring point P2, an adhesive being attached to the second anchoring point P2, any other suitable attachment mechanism, or any combination thereof. The second anchoring point P2 may be located on the target patient tissue T laterally spaced apart from the first anchoring point P1.

As shown in FIG. 15, with the tissue engagement member 104 engaging the target patient tissue T, the longitudinally downward force provided by the target patient tissue T, depicted as downward arrows in the orientation of FIG. 15, restricts the elastic material retraction strip body 102 from moving to the second condition. When the second set of tissue engagement members 110 is engaging the second anchoring point P2, the longitudinally downward force provided by both the first anchoring point P1, when engaged by the first set of tissue engagement members 106, and the second anchoring point P2 restricts the elastic material retraction strip body 102 from moving to the second condition. In other words, the elastic material retraction strip body 102 may be urged to its second condition due to the inherent properties of the elastic material. Because the elastic material retraction strip body 102 is engaged to the first anchoring point P1 of the target patient tissue T and/or the second anchoring point P2, the elastic material retraction strip body 102 provides an approximately longitudinally upward force, depicted as substantially upward arrows in FIG. 15, to the engaged tissue in order to retract the engaged tissue and move toward the second position. The engaged tissue, being attached to the surrounding patient tissue, is urged to remain in its original position. The engaged tissue provides a counteracting force, which is a longitudinally downward force, depicted as downward arrows in FIG. 15, to oppose the longitudinally upward force of the elastic material retraction strip body 102 and to prevent the retraction of the engaged tissue. This longitudinally downward force restricts the elastic material retraction strip body 102 from moving to the second condition.

Figure 16:
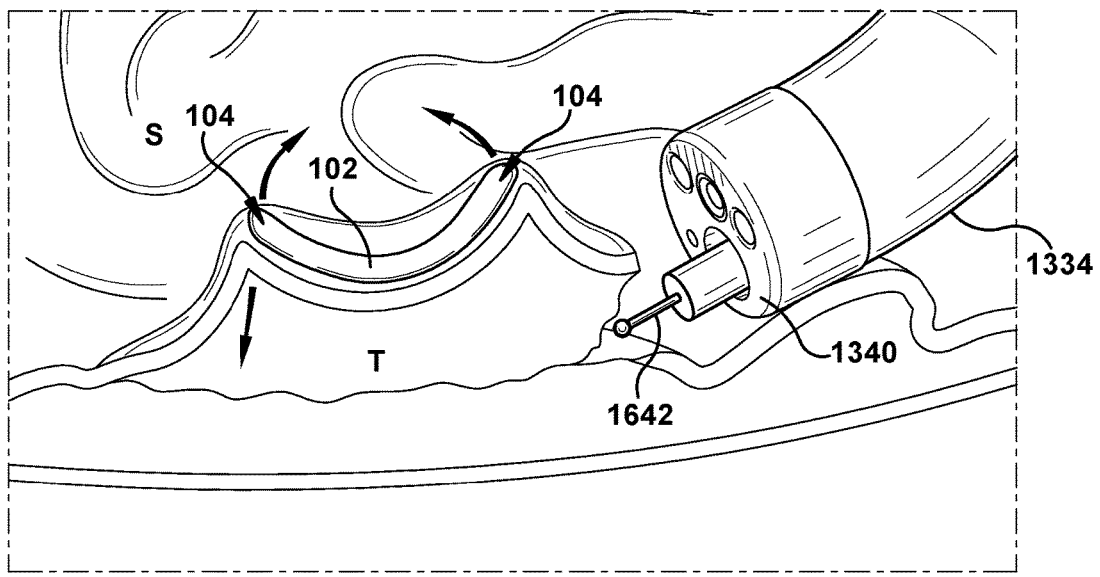

As shown in FIG. 16, a dissector 1642 may be provided to the target patient tissue site S. The dissector 1642 may be advanced to the target patient tissue site S through the endoscope lumen 1340. With the elastic material retraction strip body 102 in the first condition engaging the target patient tissue T, at least a portion of the target patient tissue T may be dissected. The dissection of the target patient tissue T responsively alleviates the longitudinally downward force provided by the target patient tissue T.

Figure 17:
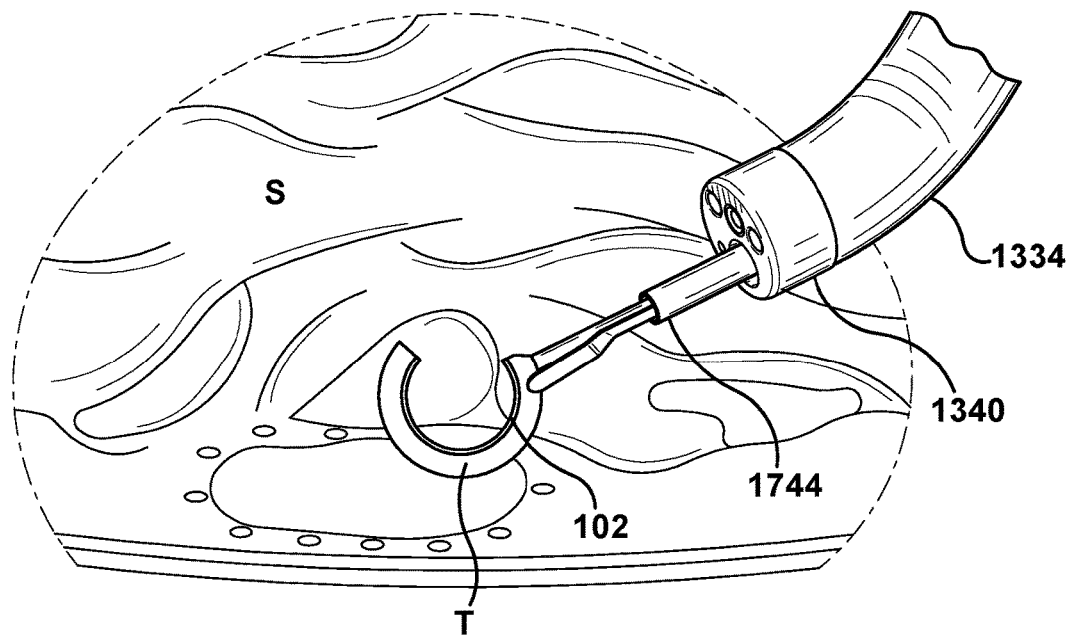

As shown in FIGS. 16-17, the target patient tissue T is selectively moved into a retracted position by selectively moving the elastic material retraction strip body 102, with the target patient tissue T attached, into the second condition. The alleviation of the longitudinally downward force provided by the target patient tissue T may prompt the retraction strip body 102 to move to the second condition in response to the inherent properties of the elastic material.

As shown in FIGS. 16-17, the selective movement of the elastic material retraction strip body 102, with the target patient tissue T attached, from the first position to the second position causes the tissue engagement member 104 to responsively move the target patient tissue T from its original position to a retracted position. The user may remove the tissue retraction device 100 with the attached, dissected target patient tissue T from the target patient tissue site S through the endoscope lumen 1340. As shown in FIG. 17, the user may use graspers 1744 to remove the tissue retraction device 100 with the attached, dissected target patient tissue T from the target patient tissue site S through the endoscope lumen 1340.

The elastic material retraction strip body 102 may be provided and used in a similar sequence largely as described above without the sheath 1020. However, without the sheath 1020, the user deforms the elastic material retraction strip body 102 to move the elastic material retraction strip body 102 to the first condition from the second condition. Further, with the elastic material retraction strip body 102 in the first condition, the elastic material retraction strip body 102 is inserted through the endoscope lumen 1340 and out to the target patient tissue site S.

The temperature responsive shape memory material retraction strip body 102 may be provided and used in a similar sequence largely as described above. However, with the temperature responsive shape memory material retraction strip body 102, the user cools the temperature responsive shape memory material retraction strip body 102 to a temperature below the transition temperature range. Once the temperature responsive shape memory material retraction strip body 102 is cooled to a temperature blow the transition temperature range, the user deforms the temperature responsive shape memory material retraction strip body 102 to the first condition from the second condition.

Further, with the temperature responsive retraction strip body 102 at the target patient tissue site S, the ambient heat at the target patient tissue site S may raise the temperature responsive shape memory material retraction strip body 102 to a temperature above the transition temperature range. When the temperature responsive shape memory material retraction strip body 102 is heated to a temperature above the transition temperature range, the inherent properties of the temperature responsive shape memory material selectively urge the temperature responsive shape memory material retraction strip body 102 toward the second condition. The alleviation of the longitudinally downward force provided by the target patient tissue T may prompt the temperature responsive shape memory material retraction strip body 102 to move to the second condition in response to the inherent properties of the temperature responsive shape memory material.

The malleable material retraction strip body 102 may be provided and used in a similar sequence largely as described above. However, with the malleable material retraction strip body 102, the user deforms the malleable material retraction strip body 102 to move the malleable material retraction strip body 102 to the first condition. The malleable material retraction strip body 102 may be selectively and manually deformed to the second condition by user manipulation of the malleable material retraction strip body 102 as the target patient tissue T is dissected.

The flexible stainless steel bistable spring band retraction strip body 102 may be provided and used in a similar sequence largely as described above. However, with the flexible stainless steel bistable spring band retraction strip body 102, the flexible stainless steel bistable spring band retraction strip body 102 may be moved into the first condition by deforming the flexible stainless steel bistable spring band retraction strip body 102 around the mandrel outer surface 1128. The radially inward force provided by the flexible stainless steel bistable spring band restricts the flexible stainless steel bistable spring band retraction strip body 102 to the mandrel outer surface 1128. As shown in FIG. 18, the mandrel 1130 with the attached stainless steel bistable spring band retraction strip body 102 may be inserted to the target patient tissue site S through the endoscope lumen 1340.

The flexible stainless steel bistable spring band retraction strip body 102 is positioned so that the tissue engagement member 104 is directly contacting at least a portion of the target patient tissue T. With the tissue engagement member 104 directly contacting at least a portion of the target patient tissue T, the mandrel 1130 is removed from at least one of the target patient tissue site S and the endoscope lumen 1340.

The target patient tissue T may be engaged by the stainless steel bistable spring band retraction strip body 102 by the user selectively applying a force to the flexible stainless steel bistable spring band retraction strip body 102 to urge the flexible stainless steel bistable spring band restriction strip body 102 to move toward the second condition. The application of force to the flexible stainless steel bistable spring band retraction strip body 102 may cause the tissue engagement feature 104 to move from the flattened condition to the flared condition. With the tissue engagement feature 104 in the flared condition, the tissue engagement feature 104 may be engaged to the target patient tissue T.

The flexible stainless steel bistable spring band restriction strip body 102 is restricted from moving to the second condition in a similar manner as described above. The alleviation of the longitudinally downward force provided by the target patient tissue T may prompt the retraction strip body 102 to move to the second condition in response to the inherent properties of the stainless steel bistable spring band.

It is contemplated that the retraction tissue device 100 may include a platform (not shown). The retraction strip body 102 is configured to be connected to and/or encapsulated within the platform. The platform may be made at least partially from a polymer. The platform may include at least one platform tissue engagement feature (not shown). The platform tissue engagement feature may be at least one of a clip, a barb, a hook, an adhesive, and any other attachment mechanism. The platform with attached retraction strip body 102 may be sized for passage through at least one of the sheath lumen 1026 and the endoscope lumen 1340.

It is contemplated that the tissue engagement feature 104 may be configured to be removably engaged to at least one of the target patient tissue T, the first anchoring point P1, and the second anchoring point P2. In this configuration, the retraction strip body 102 may be removed from at least one of the target patient tissue T, the first anchoring point P1, and the second anchoring point P2 prior to the removal of the target patient tissue T from the target patient tissue site S. The removably engaging tissue engagement feature 104 allows the retraction strip body 102 to be repositioned during the dissection of the target patient tissue T.

Figure 19:
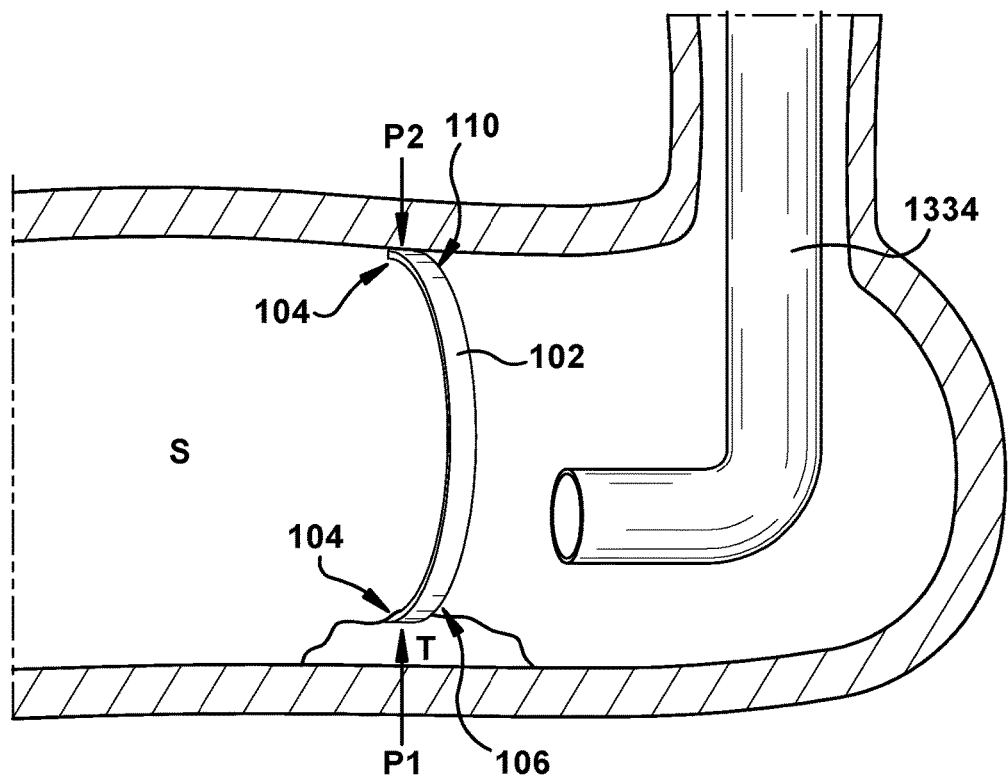
FIG. 19 illustrates an example operation feature of the aspect of FIG. 15 in an alternative arrangement.

Although the second anchoring point P2 has been shown and described above to be located on the target patient tissue T laterally spaced apart from the first anchoring point P1, it is contemplated that the second anchoring point P2, or any other desired anchoring point(s), may also or instead be oppositely facing and spaced apart from at least one of the target patient tissue T and the first anchoring point P1, as shown in FIG. 19. In such case, when the target patient tissue T is in the retracted position, the second set of tissue engagement members 110 anchors the retracted strip body 102 and dissected target patient tissue to the second anchoring point P2.

It is contemplated that the tissue retraction device 100 may assist the user in a procedure, such as, but not limited to, an endoscopic submucosal dissection. The tissue retraction device 100 may be used to retract a lesion independent of the endoscope 1334 so that the appropriate plane of dissection can be exposed without the need for a separate user-operated tissue retraction tool.

Although the tissue retraction device 100 has been described to be used in a procedure such as an endoscopic submucosal dissection, it should be understood that the tissue retraction device 100 may be used in any similar procedure that may involve the dissection, retraction, and removal of a targeted patient tissue from a patient.

Although multiple deformable material configurations have been respectively described to have certain properties and usage configurations, it should be understood that the deformable material configurations may be interchangeable in the usage configurations without harm to the tissue retraction device 100.

Although the stainless steel bistable spring band has described as being stainless steel, it should be understood that the bistable spring band may be made out of any appropriate polymer, any appropriate metal, any other appropriate material, or any combination thereof.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "preset" status may be determined at any time before the structures being manipulated actually reach that status, the desired "preset" status being made as late as immediately before the structure achieves the preset status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A system for assisting with submucosal dissections, comprising:
    a tissue retraction device having
        a retraction strip body, the retraction strip body having first and second ends spaced laterally apart, the retraction strip body being formed at least partially from a deformable material, the retraction strip body being capable of being selectively moved between a first condition, in which the retraction strip body defines a first radius of curvature between the first and second ends, and a second condition in which the retraction strip body defines a second radius of curvature between the first and second ends, such that in the first condition, the retraction strip body is capable of engaging a target patient tissue, while in the second condition, the retraction strip body is capable of exerting a tensile force on the target patient tissue to retract the target patient tissue, and
        at least two sets of tissue engagement members, a first set of tissue engagement members being located on the retraction strip body first end, a second set of tissue engagement members being located on the retraction strip body second end, the tissue engagement members being at least one of a barb, a clip, a hook, or an adhesive;
    an endoscope, the endoscope having a proximal end and a distal end, the endoscope having an endoscope lumen extending longitudinally between the endoscope proximal end and the endoscope distal end; and
    a dissector;
    wherein the deformable material is a malleable material, and the retraction strip body at least partially formed from a malleable material is capable of being selectively deformed to, and retained in, at least a selected one of the first and second conditions.

2. The system of claim 1, wherein the deformable material is an elastic material and the transition between the first and second conditions occurs responsive to at least one of an applied force and an elastic deformation of the retraction strip body.

3. The system of claim 2, wherein the deformable material is at least one of an elastic material, a shape memory material, and a fabric material, and the retraction strip body is capable of being moved into a sheath delivery condition, the retraction strip body in the sheath delivery condition is shaped to be placed within a sheath lumen of a sheath.

4. The system of claim 1, wherein the deformable material is a temperature responsive shape memory material, the retraction strip body is configured to be preset in the second condition, the retraction strip body is configured to be able to be deformed into the first condition from the second condition when the retraction strip body is at a temperature below a transition temperature range, and the retraction strip body is configured to automatically return to the second condition when the retraction strip body is at a temperature above the transition temperature range.

5. The system of claim 1, wherein the tissue retraction device has its longest dimension in the lateral direction.

6. The system of claim 1, wherein a majority of the retraction strip body is in direct contact with the target patient tissue to be dissected when in the second condition.

7. The system of claim 1, wherein the dissector is capable of operating upon a portion of the target patient tissue which is under tension due to retractive force from the retraction strip body when in the second condition.

8. The system of claim 1, wherein each set of engagement members includes at least two engagement members extending away from the retraction strip body in different directions from each other.

9. The system of claim 1, wherein the second radius of curvature is smaller than the first radius of curvature.

10. A system for assisting with submucosal dissections, comprising:
    a tissue retraction device having
        a retraction strip body, the retraction strip body having first and second ends spaced laterally apart, the retraction strip body being formed at least partially from a deformable material, the retraction strip body being capable of being selectively moved between a first condition , in which the retraction strip body defines a first radius of curvature between the first and second ends, and a second condition in which the retraction strip body defines a second radius of curvature between the first and second ends, such that in the first condition, the retraction strip body is capable of engaging a target patient tissue, while in the second condition, the retraction strip body is capable of capable of exerting a tensile force on the target patient tissue to retract the target patient tissue, and
        at least two sets of tissue engagement members, a first set of tissue engagement members being located on the retraction strip body first end, a second set of tissue engagement members being located on the retraction strip body second end, the tissue engagement members being at least one of a barb, a clip, a hook, or an adhesive;
    an endoscope, the endoscope having a proximal end and a distal end, the endoscope having an endoscope lumen extending longitudinally between the endoscope proximal end and the endoscope distal end; and
    a dissector;
    wherein the deformable material is a flexible stainless steel bistable spring band, the retraction strip body in the first condition is shaped to engage the outer surface of a mandrel, each tissue engagement member is in a flattened condition when the retraction strip body is in the first condition, and each tissue engagement member is in a flared condition when the retraction strip body is at least partially in the second condition.

11. The system of claim 10, wherein the tissue retraction device has its longest dimension in the lateral direction.

12. The system of claim 10, wherein a majority of the retraction strip body is in direct contact with the target patient tissue to be dissected when in the second condition.

13. The system of claim 10, wherein the dissector is capable of operating upon a portion of the target patient tissue which is under tension due to retractive force from the retraction strip body when in the second condition.

14. The system of claim 10, wherein each set of engagement members includes at least two engagement members extending away from the retraction strip body in different directions from each other.

15. The system of claim 10, wherein the second radius of curvature is smaller than the first radius of curvature.

* * * * *